(12) United States Patent
Debus et al.

(10) Patent No.: US 12,023,236 B2
(45) Date of Patent: Jul. 2, 2024

(54) HYBRID PROSTHESIS AND DELIVERY SYSTEM

(71) Applicant: Vascutek Limited, Renfrewshire (GB)

(72) Inventors: Sebastian Debus, Hamburg (DE); Tilo Kolbel, Hamburg (DE); Vincent Nelis, Renfrewshire (GB); Callum Cresswell, Renfrewshire (GB)

(73) Assignee: Vascutek Limited, Renfrewshire (GB)

( * ) Notice: Subject to any disclaimer, the term of this patent is extended or adjusted under 35 U.S.C. 154(b) by 0 days.

(21) Appl. No.: 17/950,605

(22) Filed: Sep. 22, 2022

(65) Prior Publication Data
US 2023/0015592 A1     Jan. 19, 2023

Related U.S. Application Data

(63) Continuation of application No. 16/331,059, filed as application No. PCT/GB2017/052602 on Sep. 6, 2017, now Pat. No. 11,458,008.

(30) Foreign Application Priority Data

Sep. 7, 2016 (GB) ..................... 1615219

(51) Int. Cl.
    *A61F 2/06*     (2013.01)
    *A61F 2/07*     (2013.01)
    *A61F 2/954*     (2013.01)

(52) U.S. Cl.
CPC ............... *A61F 2/064* (2013.01); *A61F 2/07* (2013.01); *A61F 2/954* (2013.01);
(Continued)

(58) Field of Classification Search
CPC .. A61F 2/064; A61F 2/07; A61F 2/954; A61F 2002/061; A61F 2002/065; A61F 2250/0039
See application file for complete search history.

(56) References Cited

U.S. PATENT DOCUMENTS

| 4,580,568 A | 4/1986 | Gianturco |
| 5,578,072 A | 11/1996 | Barone et al. |

(Continued)

FOREIGN PATENT DOCUMENTS

| CA | 2872125 A1 | 4/2011 |
| EP | 0880979 A1 | 12/1998 |

(Continued)

OTHER PUBLICATIONS

International Preliminary Report on Patentability for Application No. PCT/GB2021/052337 dated Mar. 23, 2023.
(Continued)

*Primary Examiner* — Katherine M Shi
*Assistant Examiner* — Mohammed S Adam
(74) *Attorney, Agent, or Firm* — Stephen J. Kenny; Foley Hoag LLP

(57) ABSTRACT

A hybrid endoprosthetic device comprises a stented tubular part and a branched tubular body connected such that a main lumen of the stented tubular part communicates with a main lumen of the branched tubular body. The branched tubular body has multiple branch lumens for connection with natural vessels of the vasculature, and includes at least one branch lumen for access to facilitate delivery and implantation of the hybrid endoprosthetic device by an endovascular step in a hybrid surgical procedure. The hybrid endoprosthetic device is configured to replace a part of the aorta and common iliac artery. A delivery system for use with the device is also disclosed.

6 Claims, 8 Drawing Sheets

(52) U.S. Cl.
CPC ... *A61F 2002/061* (2013.01); *A61F 2002/065* (2013.01); *A61F 2250/0039* (2013.01)

(56) References Cited

U.S. PATENT DOCUMENTS

| | | | |
|---|---|---|---|
| 5,824,041 | A | 10/1998 | Lenker et al. |
| 6,036,723 | A | 3/2000 | Anidjar et al. |
| 6,773,457 | B2 | 8/2004 | Ivancev et al. |
| 7,901,446 | B2 | 3/2011 | Fitzpatrick et al. |
| 8,088,155 | B1 | 1/2012 | Lauterjung |
| 8,088,159 | B2 | 1/2012 | Lauterjung |
| 8,092,511 | B2 | 1/2012 | Chuter |
| 8,486,129 | B2 | 7/2013 | Lautherjung |
| 8,652,195 | B2 | 2/2014 | Tani |
| 8,740,971 | B2 | 6/2014 | Iannelli |
| 8,968,389 | B2 | 3/2015 | Greenberg et al. |
| 9,398,964 | B2 | 7/2016 | McGee et al. |
| 9,510,936 | B2 | 12/2016 | McDonald et al. |
| 9,622,894 | B2 | 4/2017 | McGee |
| 9,788,983 | B2 | 10/2017 | Johnson et al. |
| 9,993,329 | B2 | 6/2018 | McDonald et al. |
| 10,137,021 | B2 | 11/2018 | McDonald et al. |
| 10,219,890 | B2 | 3/2019 | Madjarov et al. |
| 10,724,805 | B2 | 7/2020 | Barmeier et al. |
| 10,987,207 | B2 | 4/2021 | Wilger et al. |
| 11,026,823 | B2 | 6/2021 | McDonald et al. |
| 11,419,712 | B2 | 8/2022 | McDonald |
| 11,458,008 | B2 | 10/2022 | Debus et al. |
| 11,471,261 | B2 | 10/2022 | McDonald |
| 11,554,033 | B2 | 1/2023 | Kolbel et al. |
| 2003/0024527 | A1 | 2/2003 | Ginn |
| 2003/0120263 | A1 | 6/2003 | Ouriel et al. |
| 2003/0130720 | A1 | 7/2003 | DePalma et al. |
| 2003/0135257 | A1 | 7/2003 | Taheri |
| 2004/0117003 | A1 | 6/2004 | Ouriel et al. |
| 2004/0167618 | A1 | 8/2004 | Shaolian et al. |
| 2004/0243221 | A1 | 12/2004 | Fawzi et al. |
| 2005/0010277 | A1 | 1/2005 | Chuter |
| 2005/0033399 | A1 | 2/2005 | Richter |
| 2005/0060029 | A1 | 3/2005 | Le et al. |
| 2005/0075725 | A1 | 4/2005 | Rowe |
| 2005/0137681 | A1 | 6/2005 | Shoemaker et al. |
| 2005/0230956 | A1 | 10/2005 | Igeta |
| 2006/0054537 | A1 | 3/2006 | Cholley et al. |
| 2007/0010873 | A1 | 1/2007 | Neri |
| 2007/0106368 | A1 | 5/2007 | Vonderwalde |
| 2007/0112422 | A1 | 5/2007 | Dehdashtian |
| 2007/0135904 | A1 | 6/2007 | Eidenschink et al. |
| 2007/0168013 | A1 | 7/2007 | Douglas |
| 2008/0082159 | A1 | 4/2008 | Tseng et al. |
| 2008/0147171 | A1 | 6/2008 | Ashton et al. |
| 2009/0043330 | A1 | 2/2009 | To |
| 2009/0264991 | A1 | 10/2009 | Paul, Jr. et al. |
| 2010/0234937 | A1 | 9/2010 | Wang et al. |
| 2011/0054586 | A1 | 3/2011 | Mayberry et al. |
| 2011/0066221 | A1 | 3/2011 | White et al. |
| 2011/0190862 | A1 | 8/2011 | Bashiri et al. |
| 2011/0230956 | A1 | 9/2011 | White |
| 2012/0059448 | A1 | 3/2012 | Parker et al. |
| 2012/0071960 | A1 | 3/2012 | Tani |
| 2012/0136431 | A1 | 5/2012 | Chen |
| 2012/0158121 | A1 | 6/2012 | Ivancev et al. |
| 2012/0172887 | A1 | 7/2012 | Hatfield |
| 2012/0277849 | A1 | 11/2012 | Tani et al. |
| 2013/0131775 | A1 | 5/2013 | Hadley et al. |
| 2013/0166015 | A1 | 6/2013 | Roeder |
| 2013/0218138 | A1 | 8/2013 | Fargahi |
| 2013/0289700 | A1 | 10/2013 | Acosta-Acevedo |
| 2013/0289713 | A1 | 10/2013 | Pearson et al. |
| 2013/0325103 | A1 | 12/2013 | Arai et al. |
| 2014/0005586 | A1 | 1/2014 | Feinstein |
| 2014/0194970 | A1 | 7/2014 | Chobotov |
| 2014/0200648 | A1 | 7/2014 | Newell et al. |
| 2014/0257452 | A1 | 9/2014 | Slazas et al. |
| 2014/0277332 | A1 | 9/2014 | Slazas et al. |
| 2014/0277345 | A1 | 9/2014 | Havel et al. |
| 2014/0277359 | A1 | 9/2014 | Slazas et al. |
| 2015/0081004 | A1 | 3/2015 | Takahashi et al. |
| 2015/0105819 | A1 | 4/2015 | Becking et al. |
| 2015/0257910 | A1 | 9/2015 | Duong et al. |
| 2015/0265444 | A1 | 9/2015 | Kitaoka |
| 2016/0175132 | A1* | 6/2016 | Wilger ............... A61F 2/97 623/1.11 |
| 2017/0014221 | A1 | 1/2017 | Kelly |
| 2019/0192273 | A1 | 6/2019 | Debus et al. |
| 2019/0223996 | A1 | 7/2019 | McDonald |
| 2020/0038169 | A1 | 2/2020 | Nelis |
| 2020/0038184 | A1 | 2/2020 | McLean |
| 2020/0038211 | A1 | 2/2020 | Kolbel et al. |
| 2020/0214821 | A1 | 7/2020 | Mcdonald |
| 2021/0212846 | A1 | 7/2021 | Shahriari |
| 2021/0228330 | A1 | 7/2021 | Kelly |
| 2021/0236257 | A1 | 8/2021 | Walzman |
| 2021/0307641 | A1 | 10/2021 | Rumbles et al. |
| 2022/0273415 | A1 | 9/2022 | Brodie et al. |
| 2022/0378569 | A1 | 12/2022 | Mcdonald |
| 2023/0015592 | A1 | 1/2023 | Debus et al. |
| 2023/0119898 | A1 | 4/2023 | Kölbel et al. |
| 2023/0225853 | A1 | 7/2023 | Zeitani et al. |

FOREIGN PATENT DOCUMENTS

| | | |
|---|---|---|
| EP | 1736116 A2 | 12/2006 |
| EP | 1847236 A2 | 10/2007 |
| EP | 2606852 A1 | 6/2013 |
| EP | 2676639 A1 | 12/2013 |
| EP | 3248572 A1 | 11/2017 |
| GB | 2491477 A | 12/2012 |
| JP | H07308330 A | 11/1995 |
| JP | 2013009912 A | 1/2013 |
| JP | 2017042236 A | 3/2017 |
| RU | 2720745 C1 | 5/2020 |
| WO | WO-03/035130 A1 | 5/2003 |
| WO | WO-2004/064686 A1 | 8/2004 |
| WO | WO-2006/019626 A2 | 2/2006 |
| WO | WO-2006/088638 A1 | 8/2006 |
| WO | WO-2008/057569 A1 | 5/2008 |
| WO | WO-2008/088835 A1 | 7/2008 |
| WO | WO-2008/112270 A1 | 9/2008 |
| WO | WO-2009/009376 A2 | 1/2009 |
| WO | WO-2009/082718 A1 | 7/2009 |
| WO | WO-2009/153768 A1 | 12/2009 |
| WO | WO-2010/053563 A1 | 5/2010 |
| WO | WO-2012/043011 A1 | 4/2012 |
| WO | WO-2013/152327 A1 | 10/2013 |
| WO | WO-2014/163957 A1 | 10/2014 |
| WO | WO-2016/054537 A1 | 4/2016 |
| WO | WO-2016075615 A2 | 5/2016 |
| WO | WO-2016075615 A3 | 6/2016 |
| WO | WO-2017/136733 A1 | 8/2017 |
| WO | WO-2017/203056 A1 | 11/2017 |
| WO | WO-2018/156848 A1 | 8/2018 |
| WO | WO-2020/128417 A1 | 6/2020 |

OTHER PUBLICATIONS

European Search Report issued in European Patent Application No. 17767890.1, dated Jul. 28, 2020, 7 pages.

International Search Report and Written Opinion for Application No. PCT/GB2018/052742 dated Apr. 9, 2020 (9 pages).

International Search Report and Written Opinion for International Application No. PCT/GB2020/051617 dated Oct. 21, 2020.

International Search Report and Written Opinion issued in PCT Application No. PCT/GB2017/052916, dated Feb. 12, 2018.

International Search Report and Written Opinion of the International Searching Authority for International Application No. PCT/GB2017/052602 dated Jan. 9, 2018.

International Search Report and Written Opinion of the International Searching Authority for International Application No. PCT/GB2018/051285 dated Sep. 11, 2018.

(56) References Cited

OTHER PUBLICATIONS

International Search Report and Written Opinion of the International Searching Authority for the International Application No. PCT/GB2018/051127 dated Jul. 10, 2018.
Japanese Examination Report for JP Application No. 2019-516423 dated Jul. 27, 2021.
Levack et al., "Rapid Aortic Arch Debranching Using the Gore Hybrid Vascular Graft," Ann Thorac Surg, 95: e163-e165 (2013).
Nigro et al., "Use of the Gore Hybrid Vascular Graft in a challenging high-lying extracranial carotid artery aneurysm," J Vasc Surg, 59: 817-820 (2014).
Parodi, J.C., et al., "Transfemoral Intraluminal Graft Implantation for Abdominal Aortic Aneurysms." Annals of Vascular Surgery, vol. 5, pp. 491-499 (1991).
Search and Examination Report for Application No. GB1715658.9 dated Feb. 28, 2018 (8 pages).
Search Report dated Apr. 13, 2018 issued by the Intellectual Property Office of the United Kingdom for Application No. GB1616722.3.
Search Report dated Aug. 8, 2017 issued by the Intellectual Property Office of the United Kingdom for Application No. GB1616722.3.
Shrestha et al., "Total aortic arch replacement with a novel 4-branched frozen elephant trunk prosthesis: Single-center results of the first 100 patients," Journal of Thoracic and Cardiovascular Surgery, 152(1): 148-159 (2016).
United Kingdom Examination Report for GB Application No. 1616722.3 dated Jun. 10, 2021.
United Kingdom Search Report for GB Application No. 1706976.6 dated Jun. 22, 2021.

\* cited by examiner

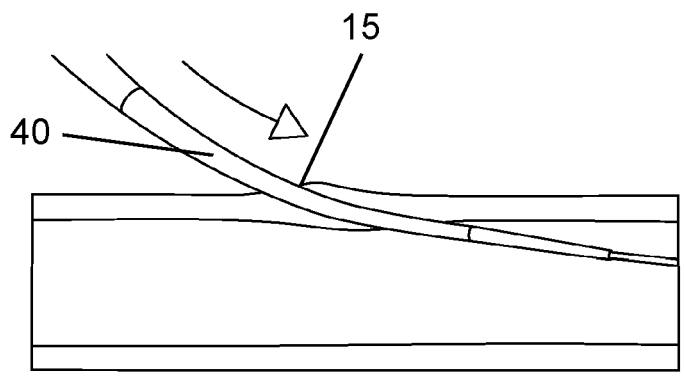
FIG. 5
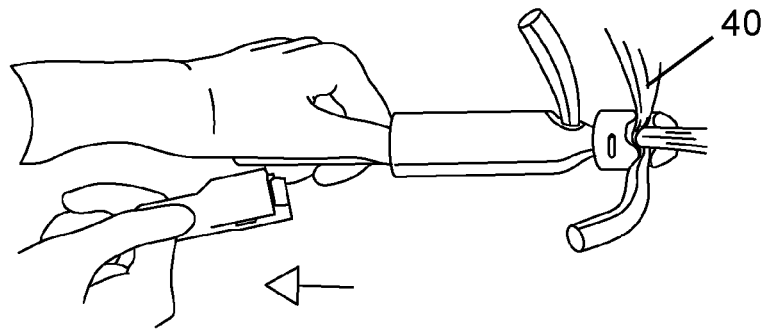
FIG. 6A
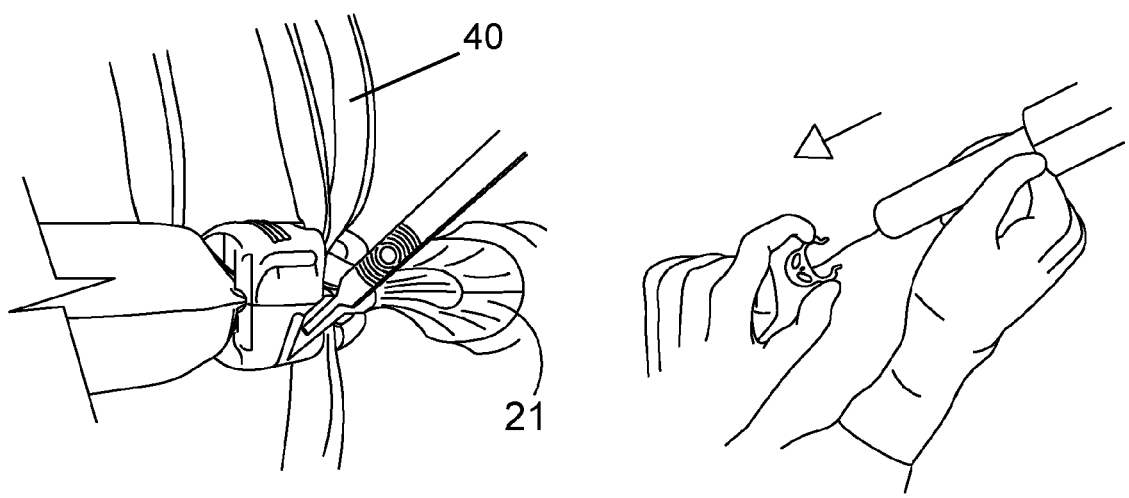
FIG. 6B                               FIG. 6C

HYBRID PROSTHESIS AND DELIVERY SYSTEM

RELATED APPLICATIONS

This application is a continuation of U.S. patent application Ser. No. 16/331,059, filed on Mar. 6, 2019, which is a U.S. National Stage Filing of International Application No. PCT/GB2017/052602, filed on Sep. 6, 2017, and published in English on Mar. 15, 2018 as WO 2018/046917, which claims priority to Great Britain Patent Application No.: 1615219.1, filed on Sep. 7, 2016. The entire teachings of the each application are hereby incorporated by reference herein.

TECHNICAL FIELD

This disclosure relates to surgical procedures and provides a prosthetic device for use as a hybrid endograft in a patient requiring surgery, particularly an intervention to treat a vascular pathology.

BACKGROUND OF THE INVENTION

Parts of the vascular system may develop degenerative defects over time, and one such defect is an aneurysm. An aneurysm is an abnormal bulge in the wall of a blood vessel leading to a localised weakening of the blood vessel wall with an increased potential for leakage, rupture and internal bleeding. The aneurysm may cause significant dilation of the natural lumen of the blood vessel compromising natural blood flow. The present disclosure relates to an endograft suitable for insertion into the aneurysm sac in the defective blood vessel to restore the vessel lumen dimensions to those of the natural blood vessel before the aneurysm developed and thereby occlude the aneurysm sac. The disclosed device is suitable for endoluminal treatment of an abdominal aortic aneurysm (AAA) or Thoracoabdominal aortic aneurysms (TAA).

Aortic aneurysms are discussed in the reference Crawford E S, Crawford J L, Safi H J, et al: Thoracoabdominal aortic aneurysms: Preoperative and intraoperative factors determining immediate and long-term results of operations in 605 patients. J Vasc Surg 3:389-404, 1986. Crawford and colleagues, recognised a correlation between aneurysm extent and clinical outcome, and proposed a classification which defines aneurysms as extent types I, II, III, and IV. Type I aneurysms involve all or most of the descending thoracic aorta and the upper abdominal aorta. Type II aneurysms involve all or most of the descending thoracic aorta and all or most of the abdominal aorta. Type III aneurysms involve the lower portion of the descending thoracic aorta and most of the abdominal aorta. Type IV aneurysms involve all or most of the abdominal aorta, including the visceral segment. Types II and III are most difficult to repair because they involve the thoracic and abdominal segments of the aorta.

Conventional methods for treatment of weakened portions of the vasculature include surgical replacement of the affected portion of the aorta, or a more conservative, minimally invasive endovascular repair.

In surgical intervention, the affected part of the blood vessel can be excised and replaced with a prosthetic graft. This invasive approach is normally performed under general anaesthesia with cardiopulmonary by-pass, so that the patient's abdomen or thorax can be opened and the prosthesis sutured in place of the aneurysmal vessel. Consequently, the method requires the time of a skilled surgeon and prolonged recovery periods for the patient in hospital. Prosthetic grafts normally used for such replacement are typically made from polyester fabric, which may be woven or knitted, and may be sealed with a sealant, for example gelatine or collagen.

More recently endovascular repair techniques have been developed in which an endovascular device is introduced using a catheter. When correctly placed in the defective natural vessel so as to bridge non-aneurysmic parts of the vessel, a stent of the endovascular device is expanded and the catheter removed. Since the catheter can be introduced via an artery, such as the femoral artery, the technique requires only minimally invasive procedures and consequently the patient should be able to recover more quickly. The procedure was first described by Parodi (Annals of Vascular Surgery vol 5, pages 491-499, 1991 and U.S. Pat. No. 5,578,072), and the technique is rapidly replacing conventional surgery as the preferred method of treating AAA and TAA.

The endovascular repair techniques use endoprosthetic devices which are placed within the patient using bespoke delivery systems designed to deliver the endoprosthetic device in a compact "packaged" form for intraluminal delivery, and including removable restraining means, allowing the endoprosthetic device to be delivered, positioned, and finally selectively deployed.

When the endoprosthetic device is deployed, the delivery system is removed, allowing the surgical procedure to be completed.

Hybrid procedures combine a conventional or modified surgical procedure with an endovascular intervention procedure and are feasible in selected high surgical risk patients. For example use of hybrid procedures provides an alternative to open repair in high risk surgical patients with complex aortic pathology.

A vascular endoprosthesis apt to exclude an aneurysmal portion of the aorta is disclosed in U.S. Pat. No. 8,740,971 B2 the content of which is incorporated herein by reference.

Whereas there is a continuing need to improve surgical procedures and endoprosthetic devices suitable for addressing patient needs, endoprosthetic devices and methods disclosed herein offer the ability to create an iliac anastomosis with reduced risk of detrimental tension whilst having sufficient scope for manoeuvre during the procedure. Additionally, the endoprosthetic devices and methods disclosed herein permit blood flow sooner than before, with the ability to expel air from an endoprosthetic device by displacement through an open ended branch lumen of the endoprosthetic device by means of blood flow into the endoprosthetic device.

SUMMARY OF THE INVENTION

Using the hybrid endoprosthetic devices disclosed herein in a known procedure or in a procedure modified as disclosed herein permits rapid perfusion of visceral arteries by retrograde blood flow whereby subsequent steps required to complete a procedure can be conducted thereafter at an acceptable pace with a foreseeable reduction in risk of ischemia or related problems normally associated with the known procedures. Therefore, the usual time pressure to complete the procedure is somewhat lessened. Significantly, the procedures described in this disclosure are designed to be carried out whilst the patient's heart remains beating, i.e. the patient is not supported on a "heart-lung" machine and so the procedure is classed as an "off-pump" procedure which offers numerous advantages.

The term "visceral arteries" is generally understood to encompass the celiac artery (celiac trunk), superior mesenteric artery (SMA), and the renal arteries. Connection of these arteries to an endoprosthetic device is provided for in the following disclosure using newly conceived devices and modifications thereof to be more particularly described herein. In particular concerns about blood losses by leakage through the delivery system are mitigated by a modification to the delivery system for the endoprosthetic device disclosed herein.

Broadly this disclosure relates to an endoprosthetic device that serves as a substitute for a deteriorated or injured part of a natural vessel, particularly the aorta-iliac region of the vasculature, and has lateral branches for connection with visceral vessels. According to aspects to be more particularly described hereinbelow, a device enabling early perfusion in a procedure is disclosed, and a modified delivery system for such a device, including a modification for improved sealing enabling reduced blood leakage during withdrawal of the delivery system is disclosed.

In the present disclosure a hybrid endoprosthetic device comprises a stented tubular part and a branched tubular body connected such that a main lumen of the stented tubular part communicates with a main lumen of the branched tubular body. Multiple branch lumens are available on the branched tubular body for connection with natural vessels or for the purpose of providing access for a surgical implement for manipulating the device, inserting a tool or ancillary device or for enabling a surgical step. The endoprosthetic device disclosed herein is suitable for use as a thoracoabdominal hybrid device. Such a device would be contemplated for relining a diseased or deformed aorta to restore a substantially normal lumen space, and also provide a substitute for the descending aorta below the diaphragm. The hybrid endoprosthetic device is configured to communicate with dependent natural vessels by provision of numerous branch lumens in an anticipated number sufficient to be able to attach a corresponding natural vessel and communicate when attached to the natural vessel with the natural lumen to allow flow of fluid therethrough. Additionally, one or more of the branch lumens can be selectively used as an access branch to facilitate delivery and implantation of the endoprosthetic device and optionally carry out steps in the surgical procedure. At least a significant part of the aorta and common iliac may be treated and partially replaced by the endoprosthetic device disclosed herein. The branched tubular body of the hybrid endoprosthetic device disclosed herein may be bifurcated to provide device limbs for respectively connecting with the iliac arteries.

The stented tubular part may be made from a fabric sleeve attached to a stent element. A physiologically inert or benign material such as a polyester may be used.

Suitable ring stents and stent elements are disclosed in GB 2 491 477 B the content of which is incorporated herein by reference.

The one or more stents may be formed from multiple windings of a shape memory material, such as Nitinol or a resilient polymer.

The ring stents may include one or more stents which have a saddle shape.

The stent element may comprise at least one circular ring stent and more than one stent which forms a saddle shape when attached within the fabric sleeve.

In other embodiments, other forms of stent can be used instead of or in combination with the aforesaid ring stents. Spiral, Z- or zig-zag, and tubular mesh types and combinations of any of these types with or without ring stents may also be suitable.

In an embodiment using ring stents having a saddle shape, these may be arranged in a series within the fabric sleeve along the longitudinal axis of the stented tubular part, so that peaks and valleys of one ring stent are aligned with corresponding peaks and valleys of other ring stents in the series of ring stents.

The stented tubular part may be provided with hooks for retention of the stented tubular part in a selected position when deployed in a lumen of a natural vessel. Suitable hooks are disclosed in U.S. Pat. No. 9,398,964 the content of which is incorporated herein by reference.

The stented tubular part may be provided with radiopaque markers to improve in vivo visualisation and to facilitate precise positioning of that part of the device. Suitable markers are disclosed in EP 1 736 116 B1 the content of which is incorporated herein by reference. The radiopaque markers may be made from a biocompatible heavy metal such as gold, platinum or tantalum, or tungsten for example, or a radiopaque ceramic contrast agent for example a ceramic bead based upon zirconia.

A collar to aid anastomosis to a natural vessel may be fixed around the hybrid endoprosthetic device at a portion thereof where the stented tubular part and branched tubular body are connected.

The branched tubular body may be connected to the stented tubular part by sewing, for example by means of a sewable collar having a flanged portion. The sewable collar is suitable for facilitating anastomosis to a natural vessel into which the endoprosthetic device penetrates such that a main lumen of the stented tubular part communicates with a main lumen of the branched tubular body to provide for blood flow through the natural vessel and the endoprosthetic device.

The branched tubular body may be made from a woven fabric.

When the "endo" part i.e. the stented tubular part is to be inserted into the lumen of a natural vessel such as the aorta, an incision in the aortic wall is made to provide an opening into which the stented tubular part can be inserted. After insertion and deployment of the stented tubular part into the natural vessel (aorta) blood flow is enabled through the lumen of the stented tubular part and into the endoprosthetic device. When blood is flowing through the hybrid endoprosthetic device the surgeon can transect the main trunk of the diseased aorta and perform an anastomosis to the collar.

The orientation of the endoprosthetic device in relation to a supine patient, where for reference purposes, the patient's head is assumed as "up" and the patient's feet are assumed as "down", is such that a favoured embodiment of the hybrid endoprosthetic device is presented uniquely as an inverted "Y" wherein the stented tubular part is directed upwardly into the thoracic aorta through a puncture below the diaphragm, and the branched tubular body is downwardly directed and presents a bifurcated part for connection with the iliac arteries.

The stented tubular part may be provided with a series of radiopaque markers along its length to enhance visualisation through an image guided delivery procedure to facilitate positioning thereof prior to deployment of the stented tubular part.

In an embodiment of a procedure for treating a patient affected by a defective natural vessel having an abnormally dilated section, an initial surgical intervention is required to prepare the patient for receiving an endoprosthetic device.

The initial surgical intervention may comprise a step of making an incision in the side wall of the defective natural vessel at the abnormal defective section to provide an opening and preparing a purse string suture surrounding that opening. The purse string suture permits the natural vessel to be subsequently closed around an inserted part of an endoprosthetic device to allow flow communication between the natural vessel and the endoprosthetic device. The natural vessel may be the thoracic aorta.

In an embodiment of a procedure for treating a patient with the endoprosthetic device, an open ended branch of the branched tubular body configured for attachment to a first patient iliac artery is attached to a side of the first patient iliac artery so that the attached branch is in flow communication therewith. A clamp is applied to the attached branch of the branched tubular body to temporarily close it. A second open ended branch of the branched tubular body configured for attachment to a second patient iliac artery remains open in an initial stage of the surgical procedure. In a subsequent stage air can be vented from the device via the second open ended branch by permitting blood flow and thereafter clamping the second open-ended branch until it is time to finally connect it to the second patient iliac branch.

In an embodiment of a procedure for treating a patient with the endoprosthetic device, the stented tubular part of the endoprosthetic device is inserted through the side wall incision prepared with a purse string sutured part of the defective natural vessel. This may be assisted by transit over an inserted guide wire or catheter substantially as used in the established Seldinger wire technique and variations thereof. Once inserted the stented tubular part of the endoprosthetic device may be deployed in an unaffected part of the natural vessel beyond the purse string suture. In such an embodiment the open lumen of the deployed stented tubular part of the endoprosthetic device can be perfused through the aorta, whilst any entrapped air is displaceable through the second open ended branch of the branched tubular body. Simultaneously, by retrograde blood flow, all visceral arteries are continuously perfused.

In an embodiment of a procedure for treating a patient with the endoprosthetic device, the visceral arteries are connectable in turn with corresponding branch lumens of the branched tubular body. Throughout the time that all of these arteries are being connected, retrograde perfusion continues through the iliac connection to the branched tubular body of the endoprosthetic device. Therefore, the risk of ischemia is remarkably diminished in comparison with prior techniques and becomes negligible to virtually nil in all foreseeable cases.

Final distal anastomosis is accomplished at a section of the aortic/iliac arteries which is not defective (not aneurysmic). The final stages may comprise distal end-to-end anastomosis of size-adjusted branches of the branched tubular body with the natural vessels by an established inlay technique. Lumbar arteries to be treated, are ligated or re-inserted into the endoprosthetic device. The treatment and re-insertion of the lumbar arteries can be facilitated by use of an open branch of the branched tubular body which serves as an access branch.

After complete attachment of the endoprosthetic device the surgical procedure can be completed by resection of the diseased or defective tissue constituting the aneurysm.

In all embodiments the delivery system for the endoprosthetic device may comprise an elongate "delivery" shaft, (or a functional equivalent such as a catheter or wire) upon which the endoprosthetic device is borne and deliverable. The delivery shaft may be inserted in a branch lumen of the endoprosthetic device, which may be a dedicated access branch on the branched tubular body of the endoprosthetic device by means of which manipulation of the device and the movement of the delivery shaft is achievable. Where a lumen guide wire is used, the elongate "delivery" shaft may be a catheter, or in the alternative the elongate "delivery" shaft is adapted to receive the guide wire through wire guides positioned on the surface of the elongate "delivery" shaft at least near the distal tip.

The elongate shaft may be malleable to enable a user to form a curvature therein to facilitate delivery if required to better suit a patient's anatomy.

The stented tubular part is delivered in a compact configuration to permit entry into a lumen and passage through the vasculature to a site requiring treatment to "normalise" the lumen of a diseased part, and the stented tubular part is subsequently deployed by expansion to permit the stented tubular part to perform its function within a lumen.

In embodiments, the delivery system comprises a retractable sheath for compactly restraining the stented tubular part to be introduced to the natural vessel during the endovascular part of the surgical procedure.

The retractable sheath may be made from a physiologically benign low friction or slip polymeric material such as polytetrafluoroethylene (PTFE). The retractable sheath may alternatively be formed from polyethyleneterephthalate (PET). The selected material should be one which is biocompatible and may be readily passed through natural vessels or artificial lumens without sticking. The retractable sheath may be surface treated, for example to impart or enhance hydrophilic properties by applying a hydrophilic coating.

Suitable polymeric flexible materials for the retractable sheath may be selected from thermoplastic polymers, elastomers, and copolymers such as nylon, polyurethane, polyethylene (PE), polytetrafluoroethylene (PTFE), expanded polytetrafluoroethylene (ePTFE), fluorinated ethylene propylene, polyether block amides (PEBA), polyimide, polyether ether ketone, and polybutylene terephthalate.

The retractable sheath may be of a multi-layered construction of flexible, polymeric materials, such as multi-layered extrusions, optionally reinforced as by use of braided layered assemblies or laminar structures incorporating bonding layers and reinforcements, or intermittent extruded composite extrusions and assemblies of variable durometer characteristics.

In embodiments the delivery system comprises a hub having a throughbore admitting an elongate delivery shaft and capable of receiving a part length of the wall of a branch of the branched tubular body, in particular cases, said branch being an access branch dedicated to the purpose of the operation of the delivery system for controlling the positioning and deployment of the endoprosthetic device.

The sheath may be designed to split (tear) in a predictable and controllable manner under application of appropriately applied force. Such force can be applied using a slitting tool which may be incorporated in the delivery system. By application of such force, the sheath may tear along its length and separate to release the stented tubular part.

In embodiments the splittable sheath is retractable against a hub comprising a splitter mechanism to facilitate removal of the retracted sheath from the stented tubular part after deployment within the natural vessel beyond the purse string suture.

In embodiments the splitter mechanism may comprise one or more passive (static) slitter elements disposed to present slitter blade edges in the proximal-distal axial direction of the delivery shaft whereby the sheath becomes split by retraction against these slitter blade edges of the passive slitter elements.

The splitter mechanism may separate the splittable sheath in one or more places, forming at least one longitudinal slit such that the sheath is removable one piece, or optionally in more than one piece, for example split longitudinally into halves.

The slitter elements may be made of a plastics material such as a polyamide, for example a nylon.

In embodiments of the splitter mechanism, a hub housing encompasses a chamber which has internal side wall surfaces in which chamber there is a throughbore for passage of an elongate delivery shaft.

The delivery shaft may be of a malleable material so that a user may shape the shaft, for example form a curvature in the shaft, prior to introduction to a patient.

In embodiments the hub housing comprises separable parts which can be fastened together about the delivery shaft and any tubular body, such as a branch lumen, that the delivery shaft has been introduced to. The hub housing separable parts may be hinged along a common edge and have fastener parts at an opposite edge. The fasteners may have snap fitting parts. A separate release clip may be applied to releasably hold the hub housing parts closed.

In alternative embodiments the hub does not comprise slitter elements attached to the hub and in these embodiments the splittable sheath is designed to be peeled or pulled apart by incorporating tear lines, perforations, pre-cut parts, or introducing sutures which facilitate separation in a controlled manner.

An option for such an embodiment lacking hub mounted slitter elements, is to provide a fine pull strand that is retrievable, passes within the splittable sheath and is attached at the distal end of the splittable sheath, for example by a suture, the pull strand returning over the splittable sheath to the proximal end, and which is thin enough to split the splittable sheath as it is withdrawn over the splittable sheath. A user pulling upon the pull strand externally from the proximal end of the pull strand lifts the distal end of the pull strand and causes the pull strand to begin splitting the splittable sheath. Continued external pull upon the pull strand by a user splits the splittable sheath from distal to proximal end. The proximal end of the splittable sheath may be attached to a pull wire or pull strap for retrieval of the split sheath.

The delivery system including the delivery shaft may be carefully withdrawn after the stented tubular part is deployed within the natural vessel beyond the purse string suture.

During the withdrawal process for removing the delivery system, there is a potential risk that blood loss may be increased due to leakage around the elongate shaft past the delivery system via the dedicated access branch on the branched tubular body.

In order to address this potential risk, any embodiment of a delivery system for an endoprosthetic device as disclosed herein may use an elongate delivery shaft modified by presence of a stopper member that is slidable axially along the length of the elongate delivery shaft and configured to fit into the hub. In operational practice during withdrawal of the elongate delivery shaft, the stopper member would be static and captive within a part of the delivery system to perform its stopper or sealing function, but the elongate delivery shaft would be freely movable relative to the stopper member. The stopper member is configured and sized to form a close fit within a branch lumen, for example part of a dedicated access branch of the branched tubular body of the endoprosthetic device borne upon the delivery shaft and contacting a part of the delivery system to form in combination therewith a fluid barrier, thereby to inhibit fluid flow by-passing the delivery shaft length to leak beyond the delivery system.

The stopper member may be a moulded part having a curved, for example part-spherical or cylindrical surface for providing a valve surface to seat within a part of the delivery system, and compress a part of a branch lumen therebetween to provide a complete seal.

The stopper member may have a compressible resilient outer surface to ensure close contact to perform its sealing function with the part of the branch lumen against a side wall of the hub throughbore. The resilient outer surfaced stopper member may be slightly oversize with respect to the width dimension of the hub throughbore to further improve sealing functionality.

The outer surface of the stopper member may comprise a silicone polymeric material.

The stopper member has a throughbore which may be lined with a material promoting slip over the delivery shaft so that sliding of the shaft relative to the stopper member is facilitated. Such materials include, PTFE and silicone-based materials such as Slick Sil® Liquid Silicone Rubber from Surface Solutions Group LLC.

In this embodiment the contacted part of the delivery system, the contacting part of the dedicated access branch of the branched tubular body, and the stopper member cooperate together to form a fluid (haemostatic) seal within the dedicated access branch during withdrawal of the delivery system. By this modification, the delivery shaft may be removed and the risk of by-pass leakage around the delivery shaft is reduced.

The contacted part of the delivery system may be upon the internal walls of the splitter chamber within the splitter mechanism, which walls may at least in part define the throughbore of the hub.

Whenever the delivery shaft is withdrawn sufficiently within the dedicated access branch, i.e. the tip of the delivery shaft is retracted towards the hub, that part of the dedicated access branch through which the tip of delivery shaft has been already withdrawn can be clamped shut. After clamping the dedicated access branch, the delivery shaft and all other parts of the delivery system can be completely removed. Final de-airing of the endoprosthetic device is achievable by unclamping the dedicated access branch which can then be closed off (sutured, fused etc.) or optionally in some cases attached to a natural vessel to provide an alternative blood flow path.

BRIEF DESCRIPTION OF THE DRAWINGS

Further details of the disclosed endoprosthetic devices and methods of use thereof are disclosed in the following description referring to the accompanying illustrative drawings in which:

FIG. 5 is a schematic side view of the insertion of the compact sheathed stented tubular part through the pursestring suture into a vessel forming part of the vasculature requiring an intervention;

FIG. 6A is a schematic illustration (external demonstration only away from a surgical site) of an initial step in manipulation of a delivery system bearing the endoprosthetic device for retraction of a sheath for the deployment of the stented tubular part when inserted into a vessel forming part of the vasculature as illustrated in FIG. 5;

FIG. 6B is a schematic illustration of a step for removing a sheath splitter mechanism from around the branched tubular body of the endoprosthetic device, and showing a deployed (expanded) stented tubular part to the right of the sheath splitter mechanism;

FIG. 6C is a schematic illustration of a step for pulling out and removing a release clip and wire;

DETAILED DESCRIPTION OF THE INVENTION

Figure 1:
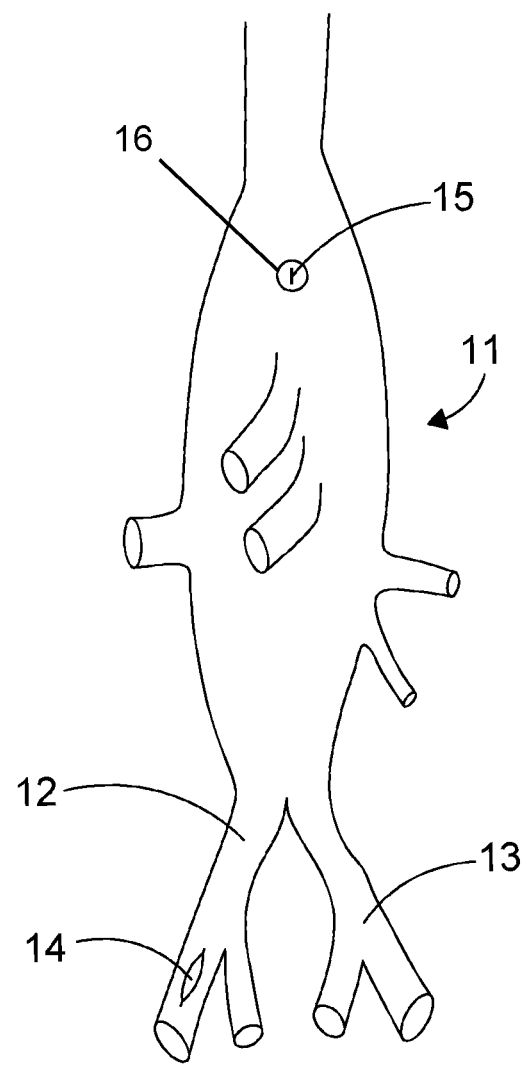
FIG. 1 is schematic side view of a defective (aneurysmic) aorta part of the vasculature and showing the minimally invasive entry point for endovascular intervention as a puncture below the diaphragm.

Description of various embodiments follows with the understanding that these are for illustrative and non-limiting disclosure purposes.

In the present disclosure, if the term "proximal" is used in relation to part of a delivery system it means the part nearest to a user of the delivery system.

The term "distal" if used herein in relation to part of a delivery system means that part farthermost from a user of the delivery system.

The term "proximal" if used herein in relation to part of an implanted endoprosthetic device means the part nearest to the heart of a patient treated with the implanted endoprosthetic device.

The term "distal" if used herein in relation to part of an implanted endoprosthetic device means the part remote from the heart of a patient treated with the implanted endoprosthetic device An embodiment similar to the endo prosthetic device disclosed herein may be used in a procedure to replace the aortic arch and to repair aneurysm and/or dissection of the descending aorta in a single surgical procedure.

An embodiment of the endoprosthetic device may comprise a stented tubular part having a main lumen of a length $L_t$, and a branched tubular body, which has multiple lumens and in a preferred embodiment is bifurcated, the branched tubular body having a length $L_b$ connected to the stented tubular part such that the overall length of the endoprosthetic device comprises length $L_t$ plus length $L_b$. The bifurcated branched tubular body may comprise substantially parallel tubular limbs extending from the stented tubular part axially with respect to a longitudinal axis through the main lumen of the stented tubular part. These substantially parallel tubular limbs are configured to be attachable to the iliac arteries of a patient.

The bifurcated branched tubular body may comprise limbs respectively of a length $Lb_1$ and $Lb_2$, where $Lb_1$ and $Lb_2$ may be the same length or of differing lengths.

The size of endoprosthetic device may be such that $L_t$ may be in the range of from 20 mm to 300 mm; and $L_b$, or $Lb_1$ and $Lb_2$ may be up to 400 mm.

Typically the branch lumens may have a length $L_{bv}$ of up to 300 mm.

The branch lumens would be designed to match patient natural vessel sizes, and may range from 4 to 20 mm in diameter. A branch lumen intended as being suitable for use as an access branch may also be from 4 to 20 mm in diameter.

In an embodiment, the deployed (in the fully opened configuration) stented tubular part may have a diameter of 12 to 50 mm. The branched tubular body may also have a diameter of 12 to 50 mm. In embodiments the branched tubular body may be of smaller diameter than the stented tubular part.

In some embodiments, the branched tubular body is tapered. For example, a taper from the stented tubular part down to the bifurcated branched tubular body of 2 to 14 mm may be required to account for geometry variation and stent oversizing etc.

The bifurcated branched tubular body may comprise tubular limbs having lumens of lesser cross-sectional dimensions than the main lumen of the stented tubular part, and the tubular limbs may have equivalent or differing cross-section dimensions in comparison of one tubular limb to the other tubular limb.

If necessary to match natural vessels in a patient, a reduction in cross-section dimensions can be achieved in the bifurcated branched tubular body by providing a tapered tubular part.

Figure 2:
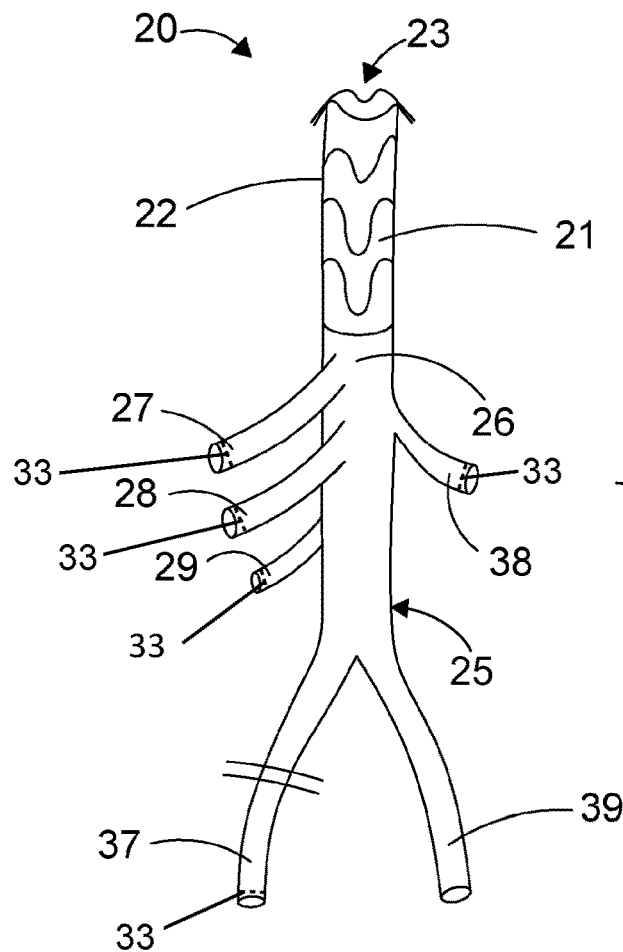
FIG. 2 is a schematic side view of an endoprosthetic device comprising an upper stented tubular part and a lower branched tubular body.
Figure 3:
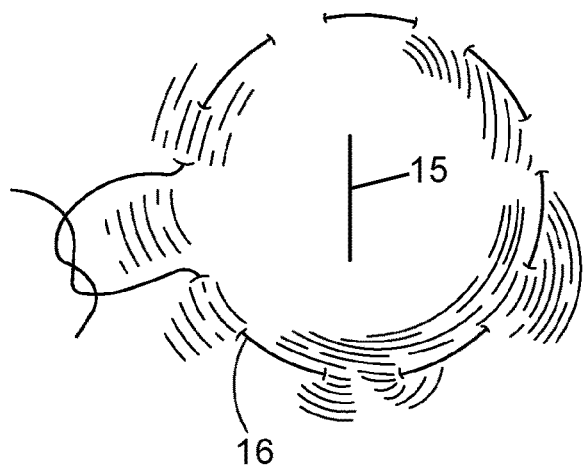
FIG. 3 is a schematic frontal view of a purse-string suture around an open end of a vessel forming part of the vasculature requiring an intervention.
Figure 4:
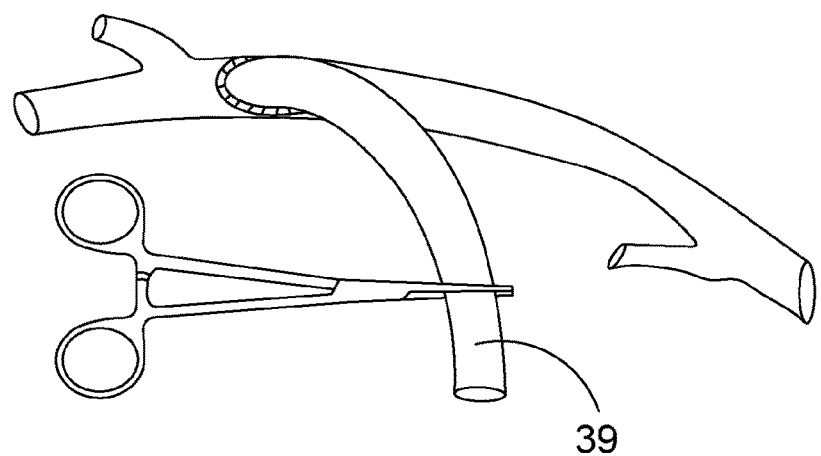
FIG. 4 is a schematic side view of an open ended and clamped branch of the branched tubular body attached to a side of the patient iliac so that the attached branch is in flow communication therewith.

Typically the natural vessels of the vasculature may differ from patient to patient in terms of size, configuration and location. Therefore the endoprosthetic device may have to be "customised" for example cut to size during the procedure or potentially the intended allocation of branches of the branched tubular body may need to be changed to compensate for unforeseen peculiarities of the unique vasculature of the patient. The endoprosthetic device may be manufactured with distal closed end or blind branches so that a choice can be made by the user of the device (surgeon, or surgical assistant) can selectively open a branch. In embodiments the distal closed end or blind branches can be created by provision of removable sutures 33 as shown in FIG. 2, or by incorporating a removable valve at the open end of respective branches of the branched tubular body.

The branched tubular body may have multiple tubular branches extending outwardly from the endoprosthetic device in a number sufficient to be attachable respectively to visceral vessels and also have at least one access branch for a minimal access surgical step, for example for insertion of an instrument or a delivery system tool and optionally for de-airing of the device during a surgical procedure. The at least one access branch may have greater lumen dimensions (length and or cross-sectional area) than any of the multiple tubular branches that would be extending laterally and attachable to visceral vessels.

More than one access branch may be provided at respectively alternative access positions on the branched tubular body.

One or more of the multiple tubular branches may be configured to extend laterally from the branched tubular body with respect to a longitudinal axis through the main lumen of the branched tubular body. This allows for lateral branch flow of blood from the main lumen of the branched tubular body to major vessels to restore vascular functionality as via any of the natural visceral vascular branches of the abdominal aorta.

The at least one access branch in any embodiment may be used for de-airing the endoprosthetic device used in a hybrid procedure during or after removal of instruments or delivery system parts and tools.

During a hybrid procedure using the endoprosthetic device disclosed herein, when the endoprosthetic device is connected to a natural vessel, particularly one of the iliac arteries, air can be vented (natural escape by displacement) through an unconnected (open) branch and perfusion is simultaneously achievable by retrograde blood flow.

In an embodiment the stented tubular part is a stent graft. The stent graft may comprise a conduit formed from a flexible sleeve attached to a rigid support or stent. The sleeve will typically be made of a fabric (usually a knitted or woven fabric) of ePTFE, PTFE or polyester, polyethylene or polypropylene and may optionally be coated to reduce friction; discourage clotting or to deliver a pharmaceutical agent. The fabric will generally be porous on at least one surface to enable cell ingrowth. The stent may be balloon-expandable (eg. a PALMAZ stent made of rigid stainless steel wire), but could also be self-expandable and formed of a shape memory material, such as nitinol (a nickel-titanium alloy). Numerous different stent designs are known in the art, for example braided stents as described in EP 0 880 979 or wire zig-zag stents as described in U.S. Pat. No. 4,580,568.

Stent grafts are commonly formed with a plurality of stents spaced along the graft. Even spacing of the stents ensures that the crush strength of the graft does not vary along its length.

However, whilst the spacing between the stents allows the graft to be curved when inserted in a body vessel, the degree of curvature is limited by the stent spacing. WO 2010/053563 describes a stent graft designed for deployment in a curved vessel. Identical stents are spaced further apart from each other in the region of the stent graft which undergoes the greatest curvature. Thus, the inter-stent spacing varies along at least part of length of the graft. However, for treatment of aneurysm, it is desirable that the stent graft exhibits a degree of stiffness across the diseased (aneurismitic) portion of the blood vessel under repair.

A suitable stent graft for an embodiment of the present hybrid endoprosthetic device may comprise a plurality of separate, unconnected ring stents, selectable from ring stent types comprising a planar circular ring, and sinusoidal- or "saddle"-shape ring stents. A saddle shape ring stent is one that when first formed is an individual circular ring stent that is normally planar, but formed of a material which is sufficiently resilient to be distorted so that a first pair of diametrically opposed points on the circumference of the ring stent are displaced in one axial direction whilst a second pair of diametrically opposed points, centrally located on the circumference between the first pair, are displaced in the opposing axial direction to form a symmetrical "saddle" shape. For convenience, the first pair of points can be described as "peaks", with the second pair of points being described as "valleys". The degree of axial displacement between the first pair of points and the second pair of points (which axial displacement is also termed the "saddle height"), is a function of the original circumference of the ring stent prior to its distortion, relative to the final circumference of a circle within which the distorted (saddle shaped) configuration can be located. Thus, the ratio of final circumference: original circumference provides a simplistic notation of the axial displacement. Generally the final circumference will be the outer circumference of the graft sleeve to which the stent is to be attached. The percentage oversize of the undistorted inner circumference of the circular stent relative to the outer circumference of the graft sleeve also gives a convenient measure of the saddle shape adopted, and can be calculated as:

$$\text{Oversize \%} = \frac{[\text{Stent inner diameter} - \text{Graft sleeve outer diameter}]}{\text{Graft sleeve outer diameter}} \times 100\%$$

Other forms of stent can be used instead of the aforesaid ring stents. Spiral, Z- or zig-zag, and tubular mesh types and combinations of any of these types with or without ring stents may also be suitable.

According to another aspect, in an embodiment of the endoprosthetic device described above, each one of the multiple branches, or a selected number of the multiple branches of the branched tubular body respectively may have a lumen that is initially closed to passage of fluid. This is achievable by forming the branch or respective branches extending from the tubular body with a distal closed or blind end. In embodiments the distal closed end or blind branches can be created by provision of removable sutures, or by incorporating a removable valve at the open end of respective branches of the branched tubular body.

Providing distal closed end branches permits improved control of perfusion through the endoprosthetic device via the connected main lumens respectively of the branched tubular part and the stented part of the endoprosthetic device. In such embodiments perfusion into the stented part of the endoprosthetic device and out one of the limbs of the bifurcated branched tubular body allows the endoprosthetic device to serve as a temporary bypass during a surgical procedure, for example to occlude an aneurysm. A selected one of the multiple branches of the branched tubular body which may have a lumen that is initially closed can be opened to serve as an access branch for a minimal access surgical or procedural step.

An advantage of use of the endoprosthetic device with initially closed end branches is that there is reduced need for extra-corporeal bypass and lessened requirement for initiating cardiac arrest because perfusion through the hybrid endoprosthetic device permits substantially continuous perfusion of the patient during the reattachment of the visceral vascular vessels to the selectively opened branches on the branched tubular body of the endoprosthetic device.

This feature of the endoprosthetic device allows for substantially normal blood pressure to be sustainable for extended periods by perfusion during the procedure.

In embodiments where multiple branches of the branched tubular body respectively have a lumen that is initially closed to passage of fluid by means of a distal closed or blind end, the said multiple branches can be selectively and sequentially opened for connection with a natural vessel, without detrimentally interrupting perfusion through the endoprosthetic device, by opening the selected distal closed or blind end, for example by removal of sutures or using a valve dedicated to the branch to be opened.

The branched tubular body may be made from a woven fabric.

An embodiment of the endoprosthetic device is configured for delivery at least in part in a compact form within a delivery system upon an elongate shaft, guide wire or catheter. An optional stopper member may be moveably mounted upon the elongate shaft, guide wire or catheter to cooperate with a clamping device which may be part of the delivery system and provide a haemostatic seal against the wall of a branch of the branched tubular body used as the access branch for the delivery system.

In an embodiment, a clamping device may be positioned over the access branch at a location where the stopper member is positioned and the clamping device is then clamped around the access branch to compress the wall of the access branch against the stopper member. This combination of cooperating parts provides a "valve mechanism" offering a haemostatic seal during a surgical procedure. Whilst the clamping device, wall of the access branch and stopper member are cooperating as a "valve mechanism", the elongate shaft, guide wire or catheter can be moved relative to the "valve mechanism" without significant loss of blood because the stopper member is moveably mounted on the elongate shaft, guide wire or catheter but restrained by the clamping device acting on the access branch to stop the stopper member from moving whilst the elongate shaft is moved.

The clamping device may comprise a hub having an axial throughbore providing a lumen admitting an elongate shaft and capable of receiving a part length of the wall of an access branch of an endoprosthetic device. The hub may comprise a rotatable collar mounted upon a threaded part of the hub and cooperating with a corresponding compressible internal part of the hub so that when the rotatable collar is turned along the threaded part, the collar and the compressible part come into contact and the compressible part reduces the dimensions of the lumen of the axial throughbore. Such reduction in dimensions of the lumen of the axial throughbore allows for compression of the part length of the wall of an access branch against the stopper member when the stopper member is appropriately positioned within the hub at the compressible part.

The hub may have an internal chamber around the axial throughbore having wall parts suitable for providing an abutment with the stopper member so that it is appropriately positioned within the hub.

The rotatable collar may be rotated manually, and may have a first lobe positioned on a surface thereof to encounter a corresponding second lobe on the hub when the rotatable collar reaches the end of the threaded part whereby applying slightly increased turning force bumps the first lobe over the second lobe to inhibit reverse rotation of the rotatable collar at the end of the threaded part. In this way after the user lets go of the rotatable collar the compression applied thereby to the compressible internal part is maintained.

A friction-reducing or slip material such as a physiologically inert or physiologically benign polymer or polymer blend may be applied as a coating on a surface of the stopper member. This surface would be at least one surface that in use makes sliding contact with the elongate shaft, guide wire or catheter. A smooth ceramic or glass coating may be used as an alternative to a polymer for slip surfaces in sliding contact with the elongate shaft, guide wire or catheter.

Useful polymeric coating materials which are flexible include polymerised hydrofluorocarbons (e.g. PTFE), and silicones.

The stopper member may be encapsulated in such a flexible reduced slip material.

In embodiments, the stopper member may be formed of a compressible but resilient material such as a silicone rubber.

A silicone rubber stopper member with a smooth silicone coating may provide a useful practical form for the purpose of forming a haemostatic seal with the access branch side wall when compressed by the clamping device.

The stopper member may have a modified surface, as by etching, to improve functionality.

The stopper member may be shaped to incorporate a groove to facilitate sliding along the elongate shaft.

An advantage of this arrangement of the juxtaposed hub, stopper member and access branch side wall, which thereby serves as a haemostatic "valve mechanism" is that the elongate shaft, guide wire or catheter used for delivery can be withdrawn until a tip of the elongate shaft, guide wire or catheter is captured within a selected portion of the access branch, an additional clamp may be applied just forward of the tip of the elongate shaft, guide wire or catheter to the access branch. This then allows the elongate shaft, guide wire or catheter to be fully withdrawn together with any delivery system components carried thereon with minimal blood loss through the access branch. Unless required for any additional procedure or for use in connection to a natural vessel, the access branch can be closed off for example by suturing close to the branched tubular body and the additional clamp removed.

A delivery system to be used for delivery of the endoprosthetic device subject of the present disclosure, comprises a malleable shaft adapted to be formed manually by a user if required to a preferred curvature whereby the malleable shaft may conform better to a patient's anatomy. The shaft may have a smooth atraumatic distal tip and a plurality of access ports located at the distal tip for receiving a guide wire to facilitate delivery of the endoprosthetic device through a natural lumen. The distal tip may have a tapered or pointed shape.

The endoprosthetic device subject of the present disclosure can be compactly packaged for delivery upon the malleable shaft of the delivery system in a manner generally known in the field by use of a removable sheath over the stented tubular part. A combination of releasable clips, fasteners and sutures can be used to hold the endoprosthetic device in a compact packaged configuration in the delivery system.

A thin sheath for constraining the stented tubular part of the endoprosthetic device upon the malleable shaft for delivery may comprise a smooth polymeric material. A polymerised hydrofluorocarbon such as PTFE is suitable.

The retractable sheath may alternatively be formed from polyethyleneterephthalate (PET). The selected material should be one which is biocompatible and may be readily passed through natural vessels or artificial lumens without sticking. The retractable sheath may be surface treated, for example to impart or enhance hydrophilic properties by applying a hydrophilic coating.

Suitable polymeric flexible materials for the retractable sheath may be selected from thermoplastic polymers, elastomers, and copolymers such as nylon, polyurethane, polyethylene (PE), polytetrafluoroethylene (PTFE), expanded polytetrafluoroethylene (ePTFE), fluorinated ethylene propylene, polyether block amides (PEBA), polyimide, polyether ether ketone, and polybutylene terephthalate.

The retractable sheath may be of a multi-layered construction of flexible, polymeric materials, such as multi-layered extrusions, optionally reinforced as by use of braided layered assemblies or laminar structures incorporating bonding layers and reinforcements, or intermittent extruded composite extrusions and assemblies of variable durometer characteristics.

An embodiment of a delivery system may further comprise a sheath removal mechanism which includes at least one slitter element for parting the sheath longitudinally to allow the constrained stented tubular part of the endoprosthetic device to expand into its deployed configuration, and a sheath removal element, such as a pull strap, cord, tape, wire or the like, connected to the sheath to allow removal of the sheath.

The slitter element may be fixed to or located within a hub that is removably mounted upon an elongate malleable delivery shaft.

The hub may comprise two part-cylindrical parts adapted to fit around the elongate delivery shaft (and guide wire when used) and be clipped or removably fastened together. Suitably the hub part-cylindrical parts can have internal surfaces configured to clamp down upon a part length of the wall of a branch of the branched tubular body used as the access branch when that part length is positioned within the hub.

In embodiments the hub may have protruding parts formed to have a slitting edge to provide a slitter element for splitting the sheath during retraction of the sheath to allow deployment of the stented tubular part of the endoprosthetic device.

The delivery system may further comprise a user manoeuvring control handle attached to one end of the elongate malleable delivery shaft remote from the distal tip to allow a user to move, manipulate and control the positioning of the delivery system, and the deployment of the endoprosthetic device to be deployed therefrom.

A unique aspect of delivery of the endoprosthetic device disclosed herein is that it is delivered in the opposite direction (retrograde insertion) from that observed in the field in the conventional so-called "elephant trunk" technique which can be used in a staged thoracic aortic surgery (Borst H G, Walterbusch G, Schaps D. Extensive aortic replacement using "elephant trunk" prosthesis. Thorac Cardiovasc Surg 1983; 31:37-40)

In an embodiment of a method involving use of the endoprosthetic device subject of the present disclosure the patient is prepared for surgery in accordance with leading standards of surgical practice and in line with good medical practice guidelines.

Following preparation of the patient and establishment of the sterile surgical field, the endoprosthetic device is presented to the surgical site using a delivery system including a hub provided with slitter elements, and at least the following steps are taken.

1. Prepare purse-string suture.
2. The iliac may be partially clamped, and an incision made. One of the limbs of the bifurcated branched tubular body serving as an iliac branch may be anastomosed to patient iliac in an end-to-side configuration. The clamp may then be released to admit blood flow into the device whereupon air in the device may be displaced from the device iliac branch and clamping is applied to the branch.
3. Insert endo stented tubular part into purse string incision below patient's diaphragm and maneuver to position the stented tubular part within the target defective natural vessel lumen, typically seeking to engage with an unaffected part of the thoracic aorta (notably this would be a retrograde/reversed insertion as compared with usual "Elephant trunk" procedure for thoracic aortic interventions).
4. Deploy endo stented tubular part of the endoprosthetic device by maneuvering the delivery system and remove the delivery system parts by taking steps including
   i. Retract the sheath over the stented tubular part, using a pull strap to bring the sheath against the hub equipped with slitter elements in the delivery system thus splitting the sheath and allowing the stented tubular part to expand to open the main lumen thereof thereby immediately admitting blood flow for perfusion through aorta.
   ii. Release each fastener, wire or any suture holding the hub and slitter elements into assembly with the endoprosthetic device and separate these parts of the delivery system.
   iii. Remove remaining delivery system locking or retention parts such as a release clip and withdraw guide wire.
   iv. Remove delivery system handle and all remaining parts of delivery system from patient.
   v. De-air implanted endoprosthetic device using access branch.
   vi. Clamp access branch and simultaneously open clamped iliac branch of bifurcated branched tubular body.
5. Attach auxiliary vessels one at a time to respectively each one of the multiple branches of the branched tubular body to perfuse visceral arteries.
6. Attach second endoprosthetic device iliac branch (second one of limbs of bifurcated branched tubular body to patient.
7. Reattach 1st iliac end-to-end.
8. Open aneurysm sac and finish operation.

In another embodiment of a surgical procedure using the presently disclosed endoprosthetic device and a delivery system including a sheath splitter comprising a hub equipped with slitter elements aligned axially with respect to a delivery shaft of the delivery system, at least the following steps are taken.

1. Prepare purse-string suture.
2. The iliac may be partially clamped, and an incision made. One of the limbs of the bifurcated branched tubular body serving as an iliac branch may be anastomosed to patient iliac in an end-to-side configuration to allow a lumen of the endoprosthetic device iliac branch to fluidly communicate with the lumen of the patient iliac for subsequent perfusion.
3. Insert endo stented tubular part into purse string incision below patient's diaphragm and maneuver to position the stented tubular part within the target defective natural vessel lumen, typically seeking to engage with an unaffected part of the thoracic aorta (notably this would be a retrograde/reversed insertion as compared with usual "Elephant trunk" procedure).
4. Deploy endo stented tubular part of the endoprosthetic device by maneuvering the delivery system and remove the delivery system parts by taking steps including
   i. Retract the sheath over the stented tubular part, using a pull strap to bring the sheath against the hub equipped with slitter elements in the delivery system thus splitting the sheath and allowing the stented tubular part to expand to open the main lumen thereof thereby immediately admitting blood flow for perfusion through the aorta.
   ii. Remove delivery system locking or retention parts such as a release clip and withdraw guide wire.
   iii. Hold hub equipped with slitter elements and retract delivery system through hub equipped with slitter elements until the delivery shaft tip is fully enclosed in the access branch.
   iv. Clamp the access branch proximal to the tip.
   v. Either cut access branch to remove the branch and delivery system from the device or cut the splitter suture and remove the splitter and delivery system while retaining the length of the access branch.
   vi. De-air device using access branch (by removing/replacing clamp).
   vii. Once de-aired, unclamp the device iliac.
5. Attach auxiliary vessels one at a time.
6. Attach 2nd iliac.
7. Reattach 1st iliac end-to-end.
8. Open aneurysm sac and finish operation.

Referring to FIG. 1, a distended aorta 11 connected with the common iliac part of the vasculature is illustrated. The bifurcation of the common iliac into first and second iliac arteries 12, 13 respectively is also illustrated. In this illustration the aorta is aneurysmic. In other circumstances the common iliac may be aneurysmic. The disclosed device is designed to treat a range of aortic and iliac aneurysm states. A minimally invasive access to the aorta is provided to the intended surgical site by way of the small incision 15 around which a purse string suture 16, as illustrated in FIG. 1 and is formed. A side entry incision 14 in an iliac artery is also made for purposes to be discussed below.

Referring to FIG. 2, a hybrid endoprosthetic device 20 comprises a stented tubular part 21 including a sleeve 22 defining a lumen 23 and a branched tubular body 25 connected such that the lumen 23 of the stented tubular part 21 communicates with a main lumen 24 of the branched tubular body 25. The branched tubular body 25 includes a first tubular body portion 26 having a length $L_t$, and a bifurcated branched tubular body 36, having a length $L_b$ extending from the first tubular body portion 26 such that the length of the branched tubular body 25 comprises length $L_t$ plus length $L_b$. The bifurcated branched tubular body 36 may comprise a pair of tubular limbs 37, 39 extending in a divergent configuration from the first tubular body portion 26 with respect to a longitudinal axis through the main lumen 24 of the first tubular body portion 26.

The bifurcated branched tubular body 36 may have limbs respectively of a length $L_{b1}$ and $L_{b2}$, where $L_{b1}$ and $L_{b2}$ may be the same length or of differing lengths.

The bifurcated branched tubular body 36 may comprise tubular limbs 37, 39 having lumens of lesser cross-section dimensions than the main lumen 24 which extends into the first tubular body portion 26, and in this embodiment the tubular limbs have equivalent cross-section dimensions in comparison of one tubular limb to the other tubular limb.

In some embodiments, a taper from the stented tubular part down to the bifurcated branched tubular body of 2-14 mm may be required to account for geometry variation and stent oversizing etc.

Figure 6D:
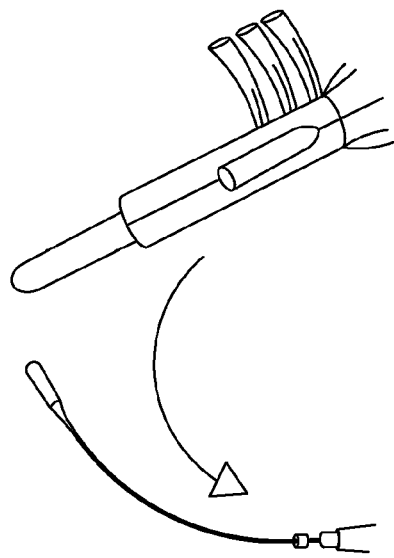
FIG. 6D is a schematic illustration of a step for pulling out and removing a handle and remainder of delivery system.
Figure 6E:
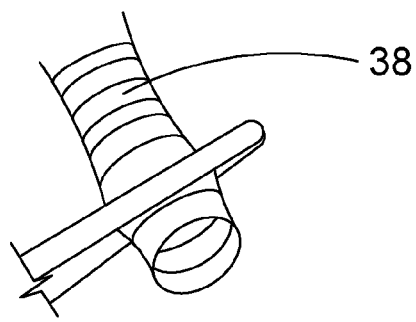
FIG. 6E is a schematic illustration of a step for using the access branch and a clamp to allow retrograde perfusion to displace air controllably from the endoprosthetic device
Figure 6F:
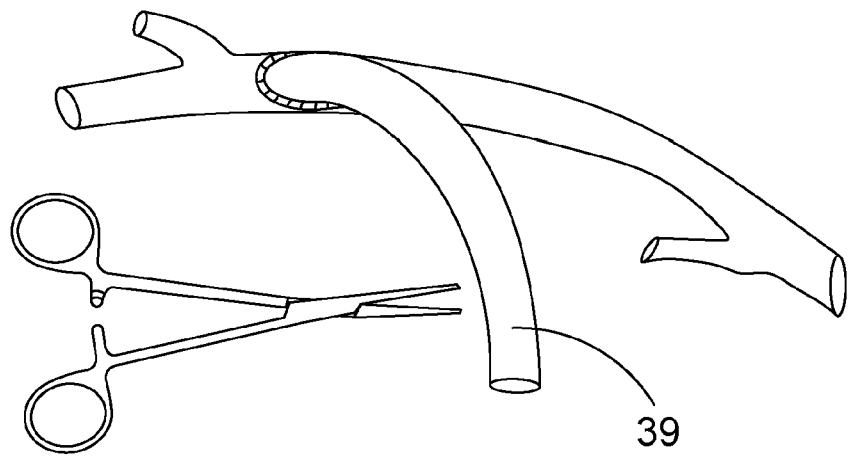
FIG. 6F is a schematic illustration of the final step of unclamping the clamped branch of the branched tubular body attached to a side of the patient iliac which is done at the same time as closing the access branch.

The illustrated branched tubular body 25 has multiple tubular branches 27, 28, 29, extending outwardly from the first tubular body portion 26 and an access branch 38 for a minimal access surgical step for introducing the stented tubular part 21, compacted within a sheath 40 into the aorta (as illustrated in FIGS. 5 and 6A) which access branch may have greater lumen dimensions (length and or cross-sectional area) than any of the multiple tubular branches 27, 28, 29.

One or more of the multiple tubular branches 27, 28, 29 may be configured to extend laterally from the first tubular body portion 26 with respect to a longitudinal axis through the first tubular body portion 26. This allows for lateral branch flow of blood from the main lumen of the branched tubular body to major vessels to restore vascular functionality as via any of the natural visceral vascular branches of the abdominal aorta The at least one access branch 38 may be used for manipulating the delivery system, de-airing the hybrid endoprosthetic device and removing the delivery system from the hybrid endoprosthetic device.

FIGS. 6A to 6E illustrate (for demonstration purposes remote from a surgical site), the steps required for retracting a sheath used to deliver the stented tubular part 21 into the aorta in a compact form, the said retraction permitting deployment of the stented tubular part 21 into the aorta, and subsequent steps for removing the delivery system and venting air from the endoprosthetic device, and use of clamps to close off the access branch 38, and allow blood flow by unclamping the iliac branch 39.

Figure 7A:
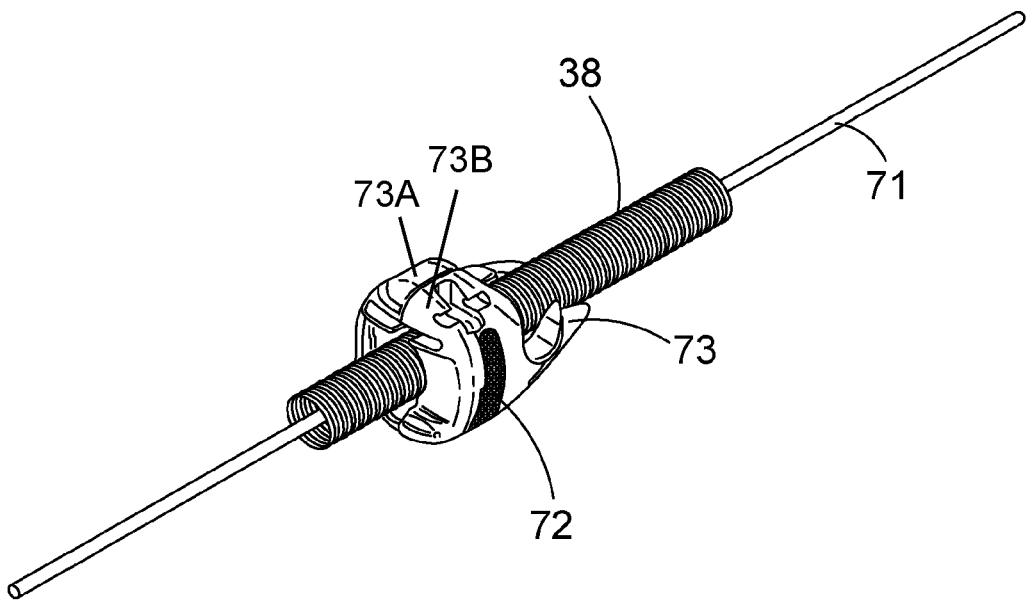
FIG. 7A is a perspective view from above and behind from the proximal end of a delivery shaft passing through a portion of the access branch of the endoprosthetic device (the remainder of which is not shown for the purposes of illustration) upon which a sheath splitter mechanism is located.
Figure 7B:
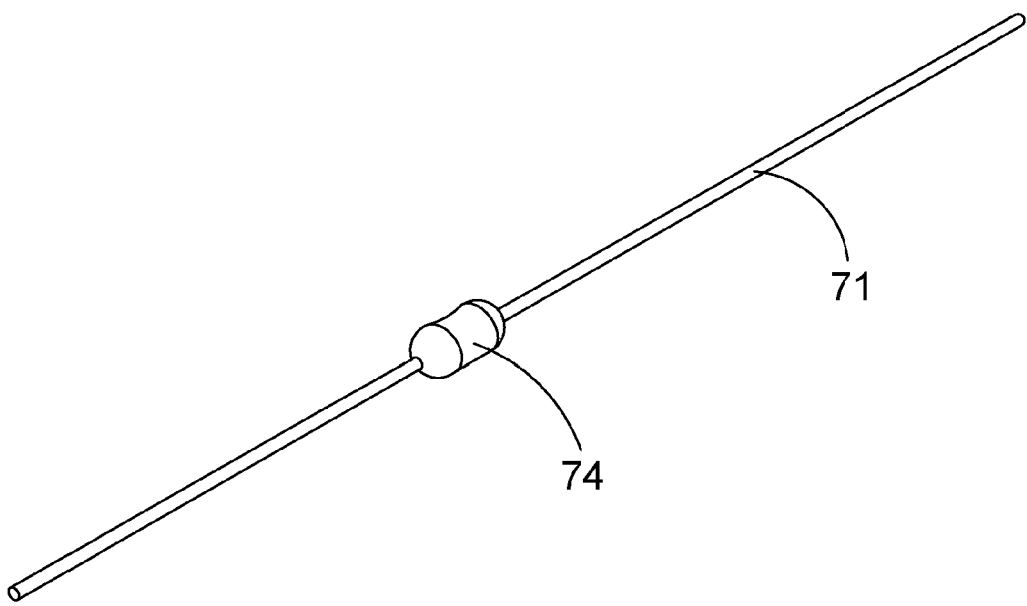
FIG. 7B is a perspective view from above and behind from the proximal end of a delivery shaft bearing a slidable stopper member that is locatable within the access branch of the endoprosthetic device and the sheath splitter mechanism shown in FIG. 7A.
Figure 7C:
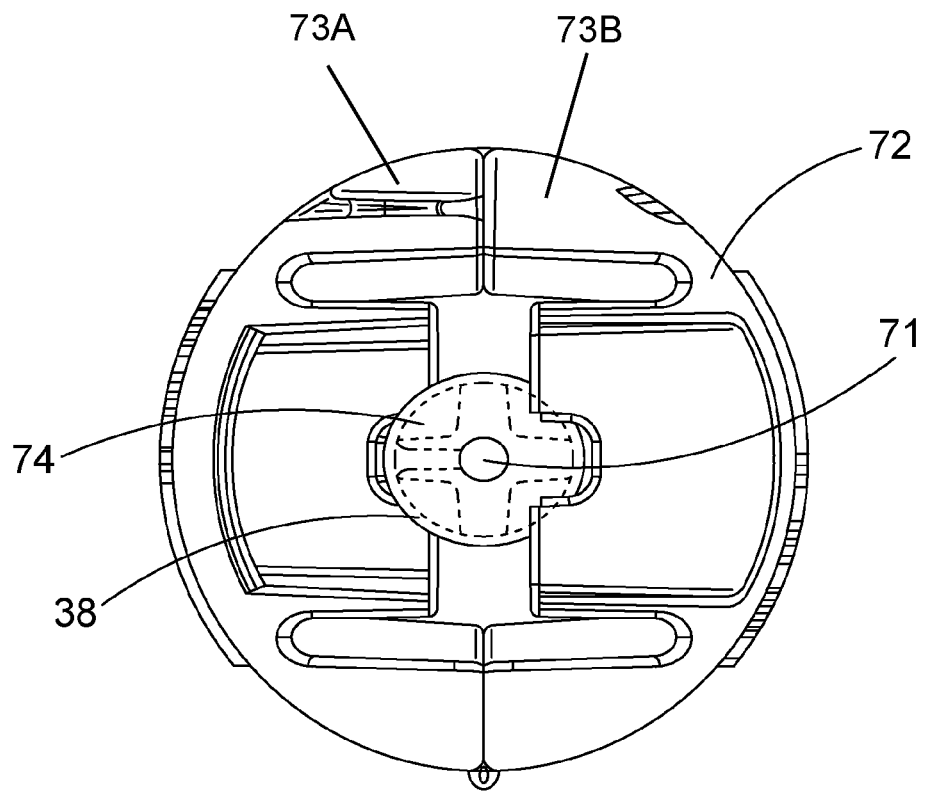
FIG. 7C is an end elevation of a sheath splitter mechanism, illustrating a splitter chamber within which internal side wall surfaces offer contact surfaces for engaging with the slidable stopper member shown in FIG. 7A.

Referring now to FIGS. 7A to 7C, an elongate malleable delivery shaft 71 is illustrated within a hub 72 including a splitter mechanism 73, the hub 72 being located around the access branch 38 shown in FIG. 7A, and a stopper member 74 is slidably mounted upon the elongate malleable delivery shaft 71 as shown in FIG. 7B without the hub 72 for illustration purposes. FIG. 7C shows an end view looking along the axial length of the elongate malleable delivery shaft 71.

Figure 8A:
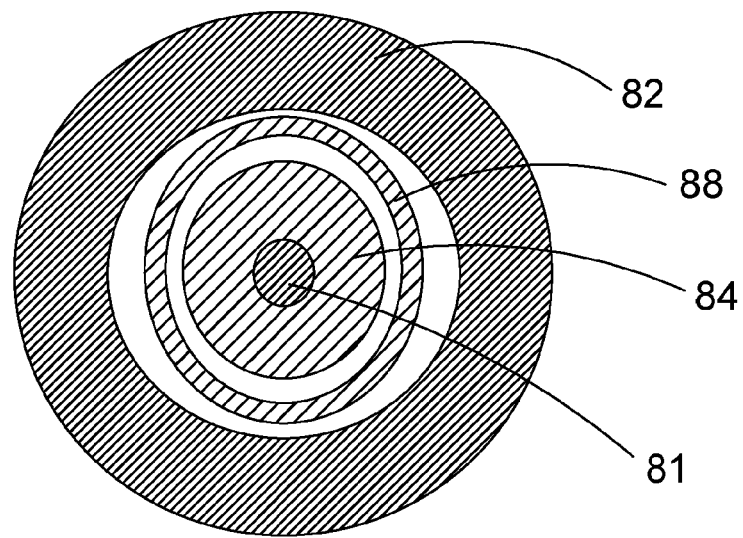
FIG. 8A is a schematic sectional view of a haemostatic seal "valve" mechanism illustrating the relative positioning of the elongate delivery shaft, stopper member and branch lumen whereby a haemostatic seal is achievable, as viewed in the longitudinal axial direction along the elongate delivery shaft.
Figure 8B:
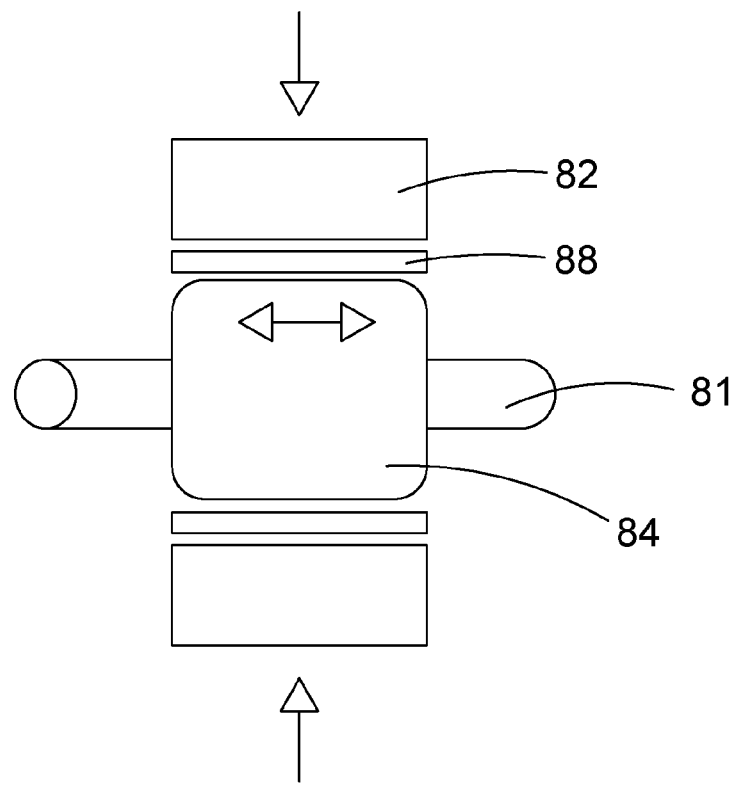
FIG. 8B is a schematic sectional view of a haemostatic seal "valve mechanism illustrating the relative positioning of the elongate delivery shaft, stopper member and branch lumen whereby a haemostatic seal is achievable, as viewed from one side of hub mounted upon the elongate delivery shaft.

Referring now to FIGS. 8A, and 8B, FIG. 8A schematically illustrates an elongate malleable delivery shaft 81 within a portion of an access branch 88, which in turn is positioned within a hub 82, and a stopper member 84 is slidably mounted upon the elongate malleable delivery shaft 81. FIG. 8B shows an end view looking along the axial length of the elongate malleable delivery shaft 81

In another embodiment of similar purpose to that illustrated in FIGS. 8A and 8B the endoprosthetic device is configured for delivery at least in part in a compact form within a delivery system upon an elongate shaft, guide wire or catheter. The delivery system includes a stopper member or sealing element which may be moveably mounted upon the elongate shaft, guide wire or catheter to cooperate with a clamping device which may be part of the delivery system. The stopper member performs a function of promoting a haemostatic seal by pressing against part of the wall of a branch of the branched tubular body used as the access branch for the delivery system, and that pressed part of the wall in turn is contacted by the clamping device.

In an embodiment, a clamping device may be positioned over the access branch at a location where the stopper member is positioned and the clamping device is then clamped around the access branch to compress the wall of the access branch against the stopper member. This combination of cooperating parts provides a "valve mechanism" offering a haemostatic seal during a surgical procedure. Whilst the clamping device, wall of the access branch and stopper member are cooperating as a "valve mechanism", the elongate shaft, guide wire or catheter can be moved relative to the "valve mechanism" without loss of blood because the stopper member is moveably mounted on the elongate shaft, guide wire or catheter but restrained by the clamping device acting on the access branch to stop the stopper member.

A friction-reducing or slip material such as a physiologically inert or benign polymer or polymer blend may be applied as a coating on a surface of the stopper member. This surface would be at least one that in use makes sliding contact with the elongate shaft, guide wire or catheter. A smooth ceramic or glass coating may be used as an alternative to a polymer for slip surfaces in sliding contact with the elongate shaft, guide wire or catheter.

Useful polymeric coating materials include polymerised hydrofluorocarbons (e.g. PTFE), and silicones.

The stopper member may be encapsulated in such a reduced slip material.

In embodiments, the stopper member may be formed of a compressible but resilient material such as a silicone rubber.

A silicone rubber stopper member with a smooth silicone coating may provide a useful practical form for the purpose of forming a haemostatic seal with the access branch side wall when compressed by the clamping device.

An advantage of this "valve mechanism" is that the elongate shaft, guide wire or catheter used for delivery can be withdrawn until a tip of the elongate shaft, guide wire or catheter is captured within a selected portion of the access branch, an additional clamp may be applied just forward of the tip of the elongate shaft, guide wire or catheter to the access branch. This then allows the elongate shaft, guide wire or catheter to be fully withdrawn together with any delivery system components carried thereon with minimal blood loss through the access branch. Unless required for any additional procedure or for use in connection to a natural vessel, the access branch can be closed off for example by suturing close to the branched tubular body and the additional clamp removed.

The hub 72 may comprise two part-cylindrical parts 73A, 73B adapted to fit around a delivery shaft 71 (and guide wire when used) and be clipped or removably fastened together. Suitably the hub part-cylindrical parts 73A, 73B can have internal surfaces configured to clamp down upon the access branch 38 when positioned therein, as shown in FIGS. 7A and 7C.

The hub may form part of a delivery system as described for embodiments hereinbefore to be used for delivery of the endoprosthetic device subject of the present disclosure.

Figure 9:
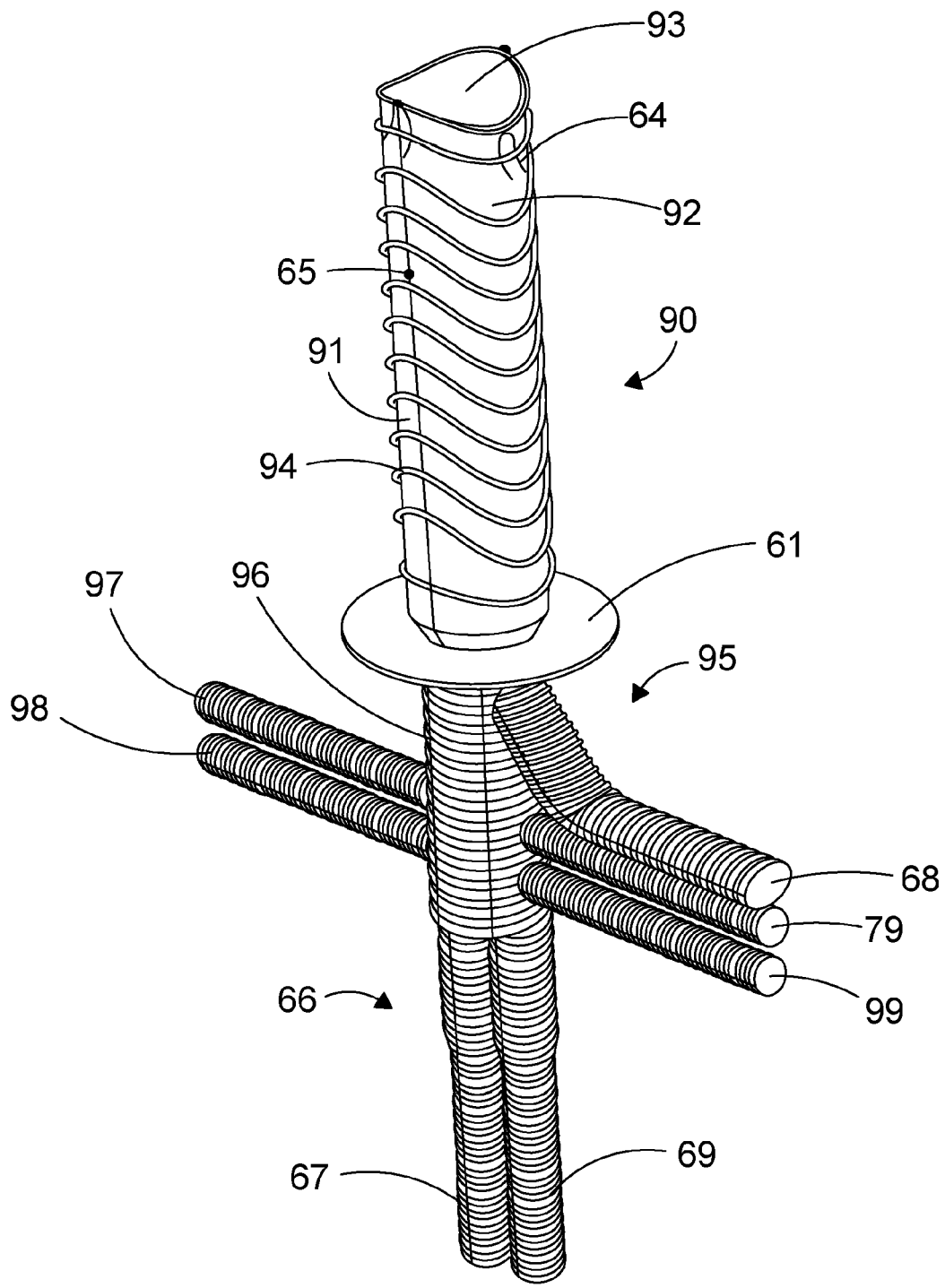
FIG. 9 is a perspective view of an embodiment of a hybrid endoprosthetic device of the invention that includes a stented tubular part having a sleeve defining a lumen and a branched tubular body, wherein the stented tubular part communicates with a main lumen of the branched tubular body.

Referring now to FIG. 9, an embodiment of the hybrid endoprosthetic device 90 comprises a stented tubular part 91 including a sleeve 92 defining a lumen 93 and a branched tubular body 95 connected such that the lumen 93 of the stented tubular part 91 communicates with a main lumen of the branched tubular body 95. The stented tubular part 91 comprises a series of ring stents 94 having a "saddle" shape. The branched tubular body 95 includes a first tubular body portion 96 having a length $L_t$, and a bifurcated branched tubular body 66, having a length $L_b$ extending from the first tubular body portion 96 such that the length of the branched tubular body 95 comprises length $L_t$ plus length $L_b$. The bifurcated branched tubular body 66 may comprise a pair of tubular limbs 67, 69 extending axially from the first tubular body portion 96 with respect to a longitudinal axis through the main lumen of the first tubular body portion 96.

The bifurcated branched tubular body 66 may have limbs respectively of a length $L_{b1}$ and $L_{b2}$, where $L_{b1}$ and $L_{b2}$ may be the same length or of differing lengths.

The bifurcated branched tubular body 66 may comprise tubular limbs 67, 69 having lumens of lesser cross-section dimensions than the main lumen which extends into the first tubular body portion 96, and in this embodiment the tubular limbs have equivalent cross-section dimensions in comparison of one tubular limb to the other tubular limb.

In some embodiments, a taper from the stented tubular part down to the bifurcated branched tubular body of 2-14 mm may be required to account for geometry variation and stent oversizing etc.

The illustrated branched tubular body 95 has multiple tubular branches 79, 97, 98, 99, extending outwardly from the first tubular body portion 96 and an access branch 68 for a minimal access surgical step for introducing the stented tubular part 91 into the aorta (as illustrated in FIG. 5) which access branch may have greater lumen dimensions (length and or cross-sectional area) than any of the multiple tubular branches 79, 97, 98, 99.

One or more of the multiple tubular branches 79, 97, 98, 99 may be configured to extend laterally from the first tubular body portion 96 with respect to a longitudinal axis through the first tubular body portion 96. This allows for lateral branch flow of blood from the main lumen of the branched tubular body to major vessels to restore vascular functionality as via any of the natural visceral vascular branches of the abdominal aorta The at least one access branch 68 may be used for manipulating the delivery system, de-airing the hybrid endoprosthetic device and removing the delivery system from the hybrid endoprosthetic device.

A collar 61 to aid anastomosis to a natural vessel is fixed around the endoprosthetic device at a portion thereof where the stented tubular part and branched tubular body are connected.

The stented tubular part is provided with hooks 64 for retention of the stented tubular part in a selected position when deployed in a lumen of a natural vessel.

The stented tubular part is provided with a radiopaque marker 65 to improve in vivo visualisation and to facilitate precise positioning of that part of the device.

All documents referred to in this specification are herein incorporated by reference. Various modifications and variations to the described embodiments of the inventions will be apparent to those skilled in the art without departing from the scope of the invention as defined in the claims. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

REFERENCE NUMERALS USED IN THE DRAWINGS 11 aorta
12 first iliac artery
13 second iliac artery
14 side entry incision in an iliac artery
15 small incision with a purse string suture
20 a hybrid endoprosthetic device
21 endo stented tubular part
22 sleeve for endo stented tubular part
23 lumen within endo stented tubular part
24 main lumen of the branched tubular body
25 branched tubular body
26 first tubular body portion of branched tubular body
27 tubular branch of branched tubular body
28 tubular branch of branched tubular body
29 tubular branch of branched tubular body
36 bifurcated branched tubular body portion of branched tubular body (FIG. 2)
37 tubular limb of bifurcated branched tubular body portion (iliac)
38 access branch of branched tubular body (FIG. 2)
39 tubular limb of bifurcated branched tubular body portion (iliac)
61 collar to aid anastomosis
64 hooks for locating endo stented tubular part in natural lumen
65 radiopaque marker
66 bifurcated branched tubular body (FIG. 9)
67 tubular limb of bifurcated branched tubular body portion (FIG. 9)
68 access branch of branched tubular body (FIG. 9)
69 tubular limb of bifurcated branched tubular body portion (FIG. 9)
71 elongate malleable delivery shaft
72 hub including a splitter mechanism
73 splitter mechanism
74 stopper member
79 tubular branch of branched tubular body (FIG. 9)
81 elongate malleable delivery shaft (FIGS. 8A & 8B)
82 hub without splitter mechanism
84 stopper member (FIGS. 8A & 8B)
88 access branch (FIGS. 8A & 8B)
90 hybrid endoprosthetic device (FIG. 9)
91 endo stented tubular part (FIG. 9)
92 sleeve for endo stented tubular part (FIG. 9)
93 lumen within sleeve for endo stented tubular part
95 branched tubular body (FIG. 9)
96 first tubular body portion (FIG. 9)
97 tubular branch of branched tubular body (FIG. 9)
98 tubular branch of branched tubular body (FIG. 9)
99 tubular branch of branched tubular body (FIG. 9)

What is claimed is:

1. A hybrid endoprosthetic delivery system, comprising:
    a) a hybrid endoprosthetic device, including
        i) a stented tubular part, having a sleeve defining a lumen, and ring stents at the sleeve,
        ii) a branched tubular body that defines a main lumen in communication with the stented tubular part, wherein the branched tubular body has a first tubular body portion defining a longitudinal axis and a bifurcated branch tubular body portion extending along the longitudinal axis from the first tubular body portion,
        iii) a plurality of tubular branches extending from the first tubular body portion, wherein the plurality of tubular branches extend laterally from the longitudinal axis of the first tubular body portion and at least one tubular branch of the plurality of tubular branches includes a removable structure forming a distal closed end, and the plurality of tubular branches disposed proximal to the bifurcated branch tubular body portion and
        iv) an access branch extending from the first tubular body portion; and
    b) a delivery device, including
        i) a delivery shaft inserted through the access branch of the hybrid endoprosthetic device, the delivery shaft having a distal tip at the stented tubular part,
        ii) a removable sheath compactly restraining the stented tubular part, and
        iii) a hub at the access branch and defining a hub throughbore through which the access branch extends;
    c) a splitter mechanism, wherein retraction of the removable sheath compactly restraining the stented tubular part by directing the removable sheath across the splitter mechanism causes the sheath to split longitudinally; and
    d) a collar at the hybrid endoprosthetic device where the branched tubular body extends from the stented tubular part.

2. The hybrid endoprosthetic delivery system of claim 1, wherein the hub includes a housing with separable parts, the separable parts fastened together about the delivery shaft.

3. The hybrid endoprosthetic delivery system of claim 2, wherein the hub housing separable parts are hingedly attached along a common edge at a hinge.

4. The hybrid endoprosthetic delivery system of claim 3, wherein the hub housing separable parts include a fastener disposed opposite the hinge.

5. The hybrid endoprosthetic delivery system of claim 4, wherein the hub housing separable parts have a snap fitting.

6. The hybrid endoprosthetic delivery system of claim 1, further comprising at least one hook disposed on the stented tubular part.

* * * * *